US006573092B1

(12) United States Patent
Kovesdi et al.

(10) Patent No.: US 6,573,092 B1
(45) Date of Patent: Jun. 3, 2003

(54) METHOD OF PREPARING A EUKARYOTIC VIRAL VECTOR

(75) Inventors: Imre Kovesdi, Rockville, MD (US); Duncan L. McVey, Derwood, MD (US)

(73) Assignee: GenVec, Inc., Gaithersburg, MD (US)

( * ) Notice: Subject to any disclaimer, the term of this patent is extended or adjusted under 35 U.S.C. 154(b) by 15 days.

(21) Appl. No.: 09/685,914

(22) Filed: Oct. 10, 2000

(51) Int. Cl.$^{7}$ ........................ C12N 15/80; C12N 15/86; C12N 15/861; C12N 15/87; C12N 15/90

(52) U.S. Cl. ................................ 435/320.1; 435/91.33; 435/91.32; 435/91.41; 435/91.42; 435/91.4; 435/325; 424/199.1; 424/205.1; 424/233.1

(58) Field of Search .............................. 435/320.1, 325, 435/91.33, 91.32, 91.41, 91.42; 424/91.4, 199.1, 205.1, 233.1

(56) References Cited

U.S. PATENT DOCUMENTS

| | | | |
|---|---|---|---|
| 5,559,099 | A | 9/1996 | Wickham et al. |
| 5,712,136 | A | 1/1998 | Wickham et al. |
| 5,736,388 | A | 4/1998 | Chada et al. |
| 5,846,782 | A | 12/1998 | Wickham et al. |
| 5,851,806 | A | 12/1998 | Kovesdi et al. |
| 5,962,311 | A | 10/1999 | Wickham et al. |
| 5,994,106 | A | 11/1999 | Kovesdi et al. |

FOREIGN PATENT DOCUMENTS

| | | | |
|---|---|---|---|
| WO | WO 95/34671 | A1 | 12/1995 |
| WO | WO 96/25506 | A1 | 8/1996 |
| WO | WO 97/00326 | A | 1/1997 |
| WO | WO 97/20051 | A1 | 6/1997 |
| WO | WO 97/21826 | A1 | 6/1997 |
| WO | WO 98/56937 | A2 | 12/1998 |
| WO | WO 99/02647 | A2 | 1/1999 |
| WO | WO 99/11764 | A | 3/1999 |
| WO | WO 99/15683 | A | 4/1999 |
| WO | WO 99/15684 | A | 4/1999 |
| WO | WO 00/14269 | A1 | 3/2000 |

OTHER PUBLICATIONS

Miyake et al. P.N.A.S. 1996, vol. 93, pp. 1320–1324.*
Brough et al., *Virology, 70,* 6497–6501 (1996).
Castro–Peralta et al., *Gene Therapy, 7,* 583–586 (2000).
Horwitz, "Adenoviruses," *in Fields Virology,* 3$^{rd}$ Edition (vol. 2), Chapter 68, 2149–2171 (Fields et al., eds.), Lippincott–Raven Publishers, New York, NY (1996).
Kojima et al., *Biochemical and Biophysical Research Communications, 246,* 868–872 (May 1998).

* cited by examiner

*Primary Examiner*—James Housel
*Assistant Examiner*—Bao Qun Li
(74) *Attorney, Agent, or Firm*—Leydig, Voit & Mayer, Ltd.

(57) ABSTRACT

The inventive method of producing a eukaryotic viral vector comprises contacting a eukaryotic cell, which comprises a unique enzyme that nicks or cleaves a DNA molecule, with a recombinant phage vector, or contacting a eukaryotic cell, which does not comprise a unique enzyme that nicks or cleaves a DNA molecule, simultaneously or sequentially, in either order, with (i) a unique enzyme that nicks or cleaves a DNA molecule, and (ii) a recombinant phage vector. The recombinant phage vector comprises the DNA molecule comprising (a) a eukaryotic viral vector genome comprising a coding sequence, (b) a phage packaging site that is not contained within the eukaryotic viral vector genome, and (c) a promoter that is operably linked to the coding sequence. The DNA molecule enters the eukaryotic cell, and the unique enzyme nicks or cleaves the DNA molecule in the eukaryotic cell in at least one region not contained within the eukaryotic viral vector genome, thereby inducing the production of and ultimately producing a eukaryotic viral vector.

21 Claims, No Drawings

METHOD OF PREPARING A EUKARYOTIC VIRAL VECTOR

TECHNICAL FIELD OF THE INVENTION

The present invention generally relates to a method of preparing a eukaryotic viral vector.

BACKGROUND OF THE INVENTION

Gene transfer to eukaryotic cells has many potential uses, both in vivo and in vitro. Gene transfer can be used, for example, to treat an animal prophylactically and/or therapeutically. Gene transfer also can be used for research purposes, such as, for example, to investigate the cellular functions of particular genes and to identify the molecular basis of specific diseases. Recombinant eukaryotic viral vectors have become a preferred method of gene transfer for many researchers and clinicians. These vectors allow for efficient and effective transfer of genes to eukaryotic cells and offer a safe method for treating animals (e.g., humans) in a clinical setting.

While researchers and clinicians have enjoyed the many advantages of eukaryotic viral vectors for gene transfer to eukaryotic cells, the difficulty of constructing stocks of these viral vectors has impeded the rate at which new and useful gene transfer experiments and protocols have been developed. Because of their large size, recombinant eukaryotic viral vectors typically are produced within a host bacterial cell via homologous recombination. The host bacterial cell typically is transfected with two or more expression vectors (e.g., plasmids) containing homologous nucleotide regions, and a double homologous recombination event occurs. Following the homologous recombination event, additional processing steps are typically required in order for the expression vector (e.g., plasmid) containing the recombinant eukaryotic vector to be actively expressed in a eukaryotic cell. These intermediate processing steps include, for example, purification of the expression vector from the bacterial cell and linearization of the vector using a restriction enzyme.

These intermediate processing steps can be both costly and time-consuming. Accordingly, there remains a need for improved methods of generating recombinant eukaryotic viral vectors which minimize, or even eliminate, the need for intermediate processing steps. The present invention seeks to provide such a method. These and other advantages of the present invention, as well as additional inventive features, will be apparent from the description of the invention provided herein.

BRIEF SUMMARY OF THE INVENTION

The invention provides a method of producing a eukaryotic viral vector. The method comprises contacting a eukaryotic cell, which comprises a unique enzyme that nicks or cleaves a DNA molecule, with a recombinant phage vector. Alternatively, the method comprises contacting a eukaryotic cell, which does not comprise a unique enzyme that nicks or cleaves a DNA molecule, simultaneously or sequentially, in either order, with (i) a unique enzyme that nicks or cleaves a DNA molecule and (ii) a recombinant phage vector. The recombinant phage vector comprises the DNA molecule comprising (a) a eukaryotic viral vector genome comprising a coding sequence, (b) a phage packaging site that is not contained within the eukaryotic viral vector genome, and (c) a promoter that is operably linked to the coding sequence. The DNA molecule enters the eukaryotic cell, and the unique enzyme nicks or cleaves the DNA molecule in the eukaryotic cell in at least one region not contained within the eukaryotic viral vector genome, whereupon a eukaryotic viral vector is produced.

DETAILED DESCRIPTION OF THE INVENTION

The present invention provides a method of producing a eukaryotic viral vector. The method comprises contacting a eukaryotic cell, which comprises a unique enzyme that nicks or cleaves a DNA molecule, with a recombinant phage vector. Alternatively, the method comprises contacting a eukaryotic cell, which does not comprise a unique enzyme that nicks or cleaves a DNA molecule, simultaneously or sequentially, in either order, with (i) a unique enzyme and (ii) a recombinant phage vector.

The recombinant phage vector comprises the DNA molecule comprising (a) a eukaryotic viral vector genome comprising a coding sequence, (b) a phage packaging site that is not contained within the eukaryotic viral vector genome, and (c) a promoter that is operably linked to the coding sequence. The DNA molecule enters the eukaryotic cell, and the unique enzyme nicks or cleaves the DNA molecule in the eukaryotic cell in at least one region outside of the eukaryotic viral vector genome, so as to induce the production of a eukaryotic viral vector. The eukaryotic viral vector is thereby subsequently produced by the eukaryotic cell.

"Nicking" is defined herein as the process of producing a single-stranded scission within a polynucleotide (e.g., a DNA molecule), i.e., the breaking of at least one phosphodiester bond within a polynucleotide, such that there is a breaking or splitting of a single strand of the polynucleotide. "Cleaving" is defined herein as the process of producing a double-stranded scission within a polynucleotide (e.g., a DNA molecule), i.e., a breaking or splitting of both strands of a polynucleotide.

Non-linear DNA molecules (e.g., plasmids and cosmids) comprising a eukaryotic viral vector genome typically must be nicked or cleaved with an enzyme prior to contacting a eukaryotic cell, in order to ensure and maximize conversion of the eukaryotic viral vector genome into a eukaryotic viral vector. It has been discovered in the context of the present invention that a recombinant phage vector comprising a DNA molecule can be used to contact (i) a eukaryotic cell comprising a unique enzyme or (ii) a eukaryotic cell that does not comprise a unique enzyme, but which is also contacted (e.g., simultaneously or sequentially, in either order) with a unique enzyme, and that the DNA molecule is nicked or cleaved within the eukaryotic cell and produced therein. Consequently, the present inventive method eliminates the need for a separate nicking or cleaving step that typically precedes the step of contacting a eukaryotic cell with the DNA molecule. The conversion of an adenoviral vector genome and the production (i.e., assembly) of an adenoviral vector within a host cell is described, for example, in Fields et al., Fields Virology, 3rd Edition (particularly Vol. 2), Lippincott-Raven Publishers, New York, N.Y. (1996).

The method of the present invention can be used to contact any suitable eukaryotic cell. A suitable eukaryotic cell can be present as a single entity or can be part of a larger group of eukaryotic cells. Suitable groups of eukaryotic cells include, for example, a eukaryotic cell culture (either mixed or pure), a tissue (e.g., epithelial tissue), an organ (e.g., heart, lung, liver, kidney, gallbladder, brain, urinary bladder, or eye), an organ system (e.g., circulatory system, respiratory system, gastrointestinal system, urinary system, nervous system, integumentary system, or other organ system), and an organism (e.g., a bird or a mammal). Suitable eukaryotic cells include, for example, cells derived from a multicellular organism, such as, a bird or a mammal, e.g., a rodent or a primate (e.g., a human), and cells of primary cell lines, e.g., HELA cells, human embryonic kidney (HEK) cells, human embryonic lung (HEL) cells, human embryonic retinoblast (HER) cells, and other cultured tissue cells. The eukaryotic cell can be, or can be derived from, anchorage-dependent cells that have the capacity to grow in suspension cultures. Moreover, the eukaryotic cell can be, or can be derived from, 293 cells, A549 cells, or modified HER cells (e.g., 911 cells and PER.C6 cells (Introgene, Inc.), which are respectively described in Fallaux et al., *Human Gene Therapy*, 7, 215–222 (1996), and International Patent Application WO 97/00326). Moreover, the eukaryotic cell can be maintained in culture in any suitable manner. Suitable manners of maintaining eukaryotic cells in culture are known to those of ordinary skill in the art.

The method of the present invention is used to contact a eukaryotic cell that supports conversion of the eukaryotic viral vector genome of the present invention into a eukaryotic viral vector. Thus, if the eukaryotic viral vector genome is deficient in a gene function essential for conversion of the eukaryotic viral vector genome into a eukaryotic viral vector, then the eukaryotic cell needs to contain DNA that complements for the gene function deficiency of the eukaryotic viral vector genome. For example, the eukaryotic cell can complement for the early region gene functions and/or late region gene functions impaired in a replication-deficient adenoviral vector genome. Moreover, the eukaryotic cell can comprise complementing genes that are arranged in a non-overlapping fashion with the eukaryotic viral vector genome, such that the likelihood of homologous recombination between the DNA molecule from the recombinant phage vector and the complementing DNA of the eukaryotic cell is reduced or eliminated. Suitable complementing eukaryotic cell lines useful in the context of the present inventive method are known in the art, as described, for example, in U.S. Pat. No. 5,851,806 (Kovesdi et al.) and Brough et al., Virol., 70, 6497–6501 (1996).

The eukaryotic cell also can comprise at least one non-native cell surface binding site or receptor (i.e., a pseudo-receptor) that binds selectively to at least one capsid (i.e., coat) protein of the recombinant phage vector. Any pseudo-receptor known to those of ordinary skill in the art that functions to increase the binding efficiency of a recombinant phage vector to a eukaryotic cell is suitable for use in the context of the present inventive method. Suitable pseudo-receptors are disclosed, for example, in International Patent Application WO 00/14269.

Any suitable method, many of which are known to those of ordinary skill in the art, can be used to modify and/or select for a eukaryotic cell that comprises a unique enzyme. Moreover, any suitable method, again many of which are known to those of ordinary skill in the art, can be used to contact a eukaryotic cell, which does not comprise a unique enzyme, with a unique enzyme, such that the unique enzyme enters the eukaryotic cell. In this regard, the unique enzyme can be present in the eukaryotic cell prior to, simultaneously, and/or after the eukaryotic cell is contacted with the recombinant phage vector. For example, the genome of the eukaryotic cell used in the context of the present inventive method can encode, and be expressed to produce, a unique enzyme, e.g., the genome of the cell can comprise at least one nucleotide sequence encoding a unique enzyme. Also, the DNA molecule of the recombinant phage vector can encode, and be expressed to produce, a unique enzyme. Moreover, a different DNA molecule, i.e., other than the DNA molecule of the recombinant phage vector, can encode, and be expressed to produce, a unique enzyme, such that the eukaryotic cell is contacted simultaneously or sequentially, in either order, with the recombinant phage vector and the DNA molecule encoding the unique enzyme. The eukaryotic cell also can be contacted with a unique enzyme that exists in the form of a polypeptide (e.g., protein).

A unique enzyme, as used in the context of the present inventive method, is defined herein as at least one unique enzyme, i.e., one or more unique enzymes. Thus, multiple unique enzymes (e.g., two or more unique enzymes, three or more unique enzymes, four or more unique enzymes, five or more unique enzymes, or even six or more unique enzymes) can be used in the context of the present invention. Moreover, the unique enzyme can be any suitable enzyme that nicks or cleaves DNA, as described, for example, in Castro-Peralta et al., *Gene Therapy*, 7, 583–586 (2000). Suitable unique enzymes include, for example, a topoisomerase (e.g., topoisomerase-1) and/or a nuclease (e.g., a DNase or an RNase). Suitable nucleases include, for example, double-strand-specific nucleases and single-strand-specific nucleases, e.g., endonucleases, exonucleases, and S1 nucleases. Suitable endonucleases include restriction enzymes, such as, for example, lambda terminase, Pac I, Asc I, Nhe I, Bam HI, and Drd I, and fusion proteins thereof.

The phrase "recombinant phage vector" is defined herein as any suitable phage vector modified to carry at least one genetic element not naturally found within the phage. Any suitable phage vector can be used in the context of the present invention. Suitable phage vectors include, for example, lambdoid phage (e.g., lambda phage and p22 phage), T-odd phage (e.g., T3 phage and T7 phage), and P1 phage. The construction of recombinant phage vectors is well understood in the art.

The recombinant phage vector needs to contact the eukaryotic cell, desirably such that the DNA molecule of the recombinant phage vector enters the eukaryotic cell. The term "contacting" is defined herein as any manner by which a peptide, polypeptide, polynucleotide (e.g., DNA molecule or RNA molecule), or vector (e.g., recombinant phage vector) is brought into close proximity with a eukaryotic cell, desirably such that the peptide, polypeptide, polynucleotide, vector, or portion thereof (e.g., the DNA molecule of the recombinant phage vector) enters the eukaryotic cell. This interaction between the eukaryotic cell and the recombinant phage vector and/or any other DNA molecule to effect entry of at least some portion of the recombinant phage vector and/or other DNA molecule (particularly, the DNA molecule of the recombinant phage vector) can be accomplished in any suitable manner.

Such contact and interaction, for example, can be effected in vitro (e.g., in an ex vivo type method or in a tissue culture study) or in vivo by electroporation, transformation, transduction, conjugation or triparental mating, (co-)transfection, (co-)infection, membrane fusion with cationic lipids, high velocity bombardment with DNA-coated microprojectiles, incubation with calcium phosphate-DNA precipitate, direct microinjection into single cells, and the like. Similarly, the recombinant phage vector and/or any other DNA molecule can be introduced into the eukaryotic cell by means of cationic lipids, e.g., liposomes. Suitable liposomes are commercially available (e.g., Lipofectin®, Lipofectamine™, and the like, supplied by Life Technologies, Gibco BRL, Gaithersburg, Md.). Moreover, liposomes having increased transfer capacity and/or reduced toxicity in vivo (see, e.g., International Patent Application WO 95/21259) can be employed in the present invention.

The aforementioned contact and interaction between the eukaryotic cell and the recombinant phage vector (particularly, to effect entry of the DNA molecule of the recombinant phage vector into the eukaryotic cell) also can be accomplished by modification of the recombinant phage vector or through use of bispecific molecules that interact with the recombinant phage vector and eukaryotic cell. These approaches also have applicability to the contact and interaction between the eukaryotic cell and any other DNA molecule so as to effect entry of that DNA molecule (or a portion thereof) into the eukaryotic cell.

Preferably, the recombinant phage vector comprises at least one capsid protein that binds to a membrane receptor on the eukaryotic cell and enables the recombinant phage vector to infect, transduce, or enter the eukaryotic cell. In this regard, the recombinant phage vector can comprise a modified coat protein. A modified coat protein, such as described in U.S. Pat. No. 5,559,099 (Wickham et al.), U.S. Pat. No. 5,712,136 (Wickham et al.), U.S. Pat. No. 5,962,311 (Wickham et al.), U.S. Pat. No. 5,846,782 (Wickham et al.), and International Patent Application WO 97/20051, can redirect the phage vector to a target cell such as one found in or obtained from a eukaryotic organism (e.g., a human). The recombinant phage vector can comprise a capsid (i.e., coat) protein that is modified to interact with a non-native, cell-surface receptor (i.e., a pseudo-receptor) of a eukaryotic cell, as described above. At the genetic level, the recombinant vector can comprise and express a nucleic acid sequence encoding a modified D capsid protein. The gene encoding the D protein can be modified by inserting DNA encoding for an amino acid sequence specific for a cell-surface structure, a receptor (including cell-surface liposaccharides and the like), an antibody, or an epitope at the amino and/or carboxyl terminus (e.g., within about 10, preferably within about 3, amino acids of either terminus). This modification process also is applicable to recombinant lambda phage, lambdoid phage, or other phage. For example, when the T7 packaging system is used, gene 10 encoding carboxy-terminally modified protein 10, or protein 10 of the T7 capsid modified at the carboxyl terminus, can be produced in the same ways that the lambda D gene product can be genetically or post-translationally modified. Most preferably, the recombinant phage vector is a lambdid vector or a eukaryotic gene transfer vector that is constructed and/or purified using the method set forth, for example, in International Patent Application WO 98/56937.

Alternatively, or in addition, the recombinant phage vector can be administered in conjunction with a bispecific molecule that binds to a capsid protein of the recombinant phage vector and to a membrane receptor of the eukaryotic cell, such that the recombinant phage vector infects the eukaryotic cell. For example, the recombinant phage vector can comprise a modified D capsid protein, as described above, that is chemically (e.g., covalently) or transiently (e.g., through biological interactions comprising hydrophobic, ionic or electrostatic, and/or Van der Waal interactions using, for example, an antibody) modified by a bispecific molecule having affinity for the phage coat protein (whether modified or not) and (i) a cell surface structure, (ii) a receptor (including cell surface liposaccharides and the like), (iii) an antibody, or (iv) an epitope, as described, for example, in U.S. Pat. No. 5,712,136 (Wickham et al.).

The DNA molecule can exist in any suitable form in the recombinant phage vector. For example, the DNA molecule can exist in a circular form in the recombinant phage vector. Alternatively, the DNA molecule can exist in a linear form.

The DNA molecule of the recombinant phage vector comprises a eukaryotic viral vector genome. The eukaryotic viral vector genome can be any suitable eukaryotic viral vector genome. The eukaryotic viral vector genome can comprise a eukaryotic viral amplicon, e.g., an amplicon comprising an ITR and any suitable origin of replication. Preferably, the eukaryotic viral vector genome is an adenoviral vector genome. The adenoviral vector genome can be of any serotype of adenovirus, e.g., adenoviral serotypes 1 through 51, which are currently available from the American Type Culture Collection (ATCC, Manassas, Va.), or from any other serotype of adenovirus. For instance, the adenovirus can be of subgroup A (e.g., serotypes 12, 18, and 31), subgroup B (e.g., serotypes 3, 7, 11, 14, 16, 21, 34, and 35), subgroup C (e.g., serotypes 1, 2, 5, and 6), subgroup D (e.g., serotypes 8, 9, 10, 13, 15, 17, 19, 20, 22–30, 32, 33, 36–39, and 42–47), subgroup E (serotype 4), subgroup F (serotypes 40 and 41), or any other adenoviral serotype. Preferably, the adenovirus is of subgroup C, particularly of serotype 2 or 5. However, the adenovirus can be a non-group C adenovirus. Non-group C adenoviral vectors, methods of producing non-group C adenoviral vectors, and methods of using non-group C adenoviral vectors are disclosed in, for example, U.S. Pat. Nos. 5,801,030 (McVey et al.), 5,837,511 (Falck-Pedersen et al.), and 5,849,561 (Falck-Pedersen et al.), and International Patent Applications WO 97/12986 and WO 98/53087.

The eukaryotic viral vector preferably is an adenoviral vector that is deficient in at least one gene function (e.g., one, two, three, or more gene functions) required for viral replication (i.e., an essential gene function), thereby resulting in a "replication-deficient" adenoviral vector. Preferably, the adenoviral vector has at least one deficiency in one or more early regions of the adenoviral genome. For example, the adenoviral vector can be deficient in at least one essential gene function of the E1 or E4 region of the adenoviral genome (e.g., to form an $E1^-$ or $E1^-E4^-$ adenoviral vector). With respect to the E1 region, the adenoviral vector can be deficient in at least one essential gene function of the E1a region and/or at least part one essential gene function of the E1b region (e.g., an $E1a^-E1b^-$ adenoviral vector). The E3 region of the adenoviral genome is not essential for viral replication, and an adenoviral vector can have an E3 region which has been deleted, in whole or in part, alone or in conjunction with essential gene function deficiencies (e.g., to form an $E1^-E3^-$ or $E1a^-E1b^-E3^-$ adenoviral vector). In addition, the adenoviral vector can have a mutation in the major late promoter (MLP). The mutation in the MLP can be in any of the MLP control elements such that it alters the responsiveness of the promoter, as discussed in International Patent Application WO 00/00628.

The adenoviral vector can be "multiply deficient," meaning that the adenoviral vector is deficient in one or more essential gene functions required for viral replication in each of two or more regions, such as the E1 (e.g., E1a and/or E1b), E2 (e.g., E2a), and/or E4 regions, optionally in addition to a partial or complete deletion of the non-essential E3 region. For example, the aforementioned $E1^-$ deficient or $E1^-$, $E3^-$ deficient adenoviral vectors can be further deficient in at least one essential gene function of the E4 region (e.g., to form an $E1^-E4^-$ or $E1^-E3^-E4^-$ adenoviral vector). Alternatively, the eukaryotic viral vector genome can be an adenoviral vector that is deficient in at least one essential gene function of the E1 and E2 regions (e.g., lacks all or part of the E1 region and all or part of the E2 region to form an $E1^-E2^-$ adenoviral vector). Other suitable adenoviral vectors include adenoviral vectors, preferably replication-deficient adenoviral vectors, lacking all or part of the E1 region, all or part of the E2 region, and all or part of the E3 region (i.e., $E1^-E2^-E3^-$ adenoviral vectors), adenoviral vectors lacking all or part of the E1 region, and all or part of the E2 region, and all or part of the E4 region (i.e., $E1^-E2^-E4^-$ adenoviral vectors), and adenoviral vectors lacking all or part of the E1 region, all or part of the E2 region, all or part of the E3 region, and all or part of the E4 region (i.e., $E1^-E2^-E3^-E4^-$ adenoviral vectors). Suitable replication-deficient adenoviral vectors are disclosed in U.S. Pat. Nos. 5,851,806 (Kovesdi et al.) and 5,994,106 (Kovesdi et al.) and International Patent Applications WO 95/34671 and WO 97/21826.

The eukaryotic viral vector genome comprises a coding sequence. The coding sequence is defined herein as at least one coding sequence (i.e., one or more coding sequences). Thus, multiple coding sequences (e.g., two or more coding sequences, three or more coding sequences, four or more coding sequences, six or more coding sequences, or even eight or more coding sequences) can be used in the context of the present invention. The coding sequence can encode, and be expressed to produce, any suitable polynucleotide (e.g., cDNA molecule, mRNA molecule, catalytic RNA molecule, or antisense RNA molecule), polypeptide (e.g., chimeric protein), or combination thereof. Suitable coding sequences include any coding sequence that is normally present in the eukaryotic viral vector genome (i.e., endogenous to the eukaryotic virus from which the eukaryotic viral vector genome is derived) or, more typically, that is not normally present in the eukaryotic viral vector genome (i.e., not endogenous to the eukaryotic virus from which the eukaryotic viral vector genome is derived). For example, the coding sequence can encode and be expressed to produce any prophylactic, therapeutic, diagnostic, and/or marker polynucleotide and/or polypeptide. Preferably, expression of the coding sequence does not result in the death of the cell in which it is expressed, unless that is the desired result. Preferred coding sequences include, for example, coding sequences for vascular endothelial growth factor (VEGF, particularly $VEGF_{121}$, $VEGF_{145}$, $VEGF_{165}$, and $VEGF_{189}$), tumor necrosis factor (TNF, particularly TNF-$\alpha$), an inducible nitric oxide synthase (iNOS), pigment epithelium derived factor (PEDF), ciliary neurotrophic factor (CNTF), atonal-associated peptides (e.g., mouse atonal homolog-1 (Math-1) or human atonal homolog-1 (Hath-1)), or combinations thereof.

The DNA molecule of the recombinant phage vector also comprises a phage packaging site. The phage packaging site can be any suitable phage packaging site. In this regard, any phage packaging site (many of which are known to those of ordinary skill in the art) which functions to package a DNA molecule into a phage head suitable for use in the context of the present inventive method can be used. When the DNA molecule exists in a linear form, the phage packaging site can exist as two phage packaging ends that are situated at, or in close proximity to, the terminal ends of the DNA molecule. Preferred phage packaging ends include, for example, a lambda phage cohesive (cos) site and a P1 packaging site.

The DNA molecule of the recombinant phage vector further comprises a promoter (i.e., a regulatory sequence). The promoter can be any suitable promoter. At least one promoter, i.e., one or more promoters, is contained within the DNA molecule (usually but not necessarily within the eukaryotic viral vector genome) and is operably linked to at least one coding sequence within the eukaryotic viral vector genome.

Any promoter (i.e., whether isolated from nature or produced by recombinant DNA or synthetic techniques) can be used in the context of the present invention to provide for transcription of the coding sequence. A promoter can be native or non-native to the coding sequence to which it is operably linked. The promoter desirably directs transcription in a eukaryotic (desirably mammalian) cell. As is known to those of ordinary skill in the art, suitable promoter regions can vary in length and sequence and can further encompass one or more DNA binding sites for sequence-specific DNA binding proteins that modulate promoter activity.

Preferably, the promoter is a viral promoter. Suitable viral promoters are known in the art and include, for example, cytomegalovirus (CMV) promoters (e.g., a CMV immediate-early promoter), promoters derived from human immunodeficiency virus (HIV) (e.g., an HIV long terminal repeat promoter), Rous sarcoma virus (RSV) promoters (e.g., an RSV long terminal repeat promoter), an adenoviral promoter (e.g., the Ad2 or Ad5 major late promoter and tripartite leader), mouse mammary tumor virus (MMTV) promoters, HSV promoters (e.g., a herpes thymidine kinase promoter, as disclosed, for example, in Wagner et al., *Proc. Natl. Acad. Sci.*, 78, 144 (1981)), promoters derived from SV40 or Epstein Barr virus, and the like, and hybrids thereof (e.g., a CMV-RSV hybrid promoter).

Many of the above-identified viral promoters are constitutive promoters. Such promoters, as well as mutations thereof, are known and are described in the art (see, e.g., Boshart et al., *Cell*, 41, 521–530 (1985)). Suitable promoters for transcription of the coding sequence also include regulatable promoters, such as, for example, promoters that are up-regulated and/or down-regulated in response to appropriate signals. For instance, a promoter can be inducible by at least one transcriptional activator (e.g., a cis-activator or a trans-activator) and/or repressible by at least one transcriptional repressor (e.g., a cis-repressor or a trans-repressor). A cis-regulator is defined herein as any suitable activator (i.e., cis-activator) or repressor (i.e., cis-repressor) encoded for by a portion of the DNA molecule of the recombinant phage vector. A trans-regulator is defined herein as any suitable activator (i.e., trans-activator) or repressor (i.e., trans-repressor) encoded for by a polynucleotide that is distinct from the DNA molecule of the recombinant phage vector. Moreover, a promoter can be inducible and/or repressible by an exogenous agent, such as, for example, a drug or an administered protein. A promoter also can be inducible and/or repressible by at least one molecule (e.g., protein) of a cell with which the recombinant phage vector or DNA molecule thereof is contacted. In this regard, a promoter can be a tissue-specific promoter, i.e., a promoter that is preferentially induced and/or repressed in a particular tissue. Examples of suitable regulatable promoter systems include, but are not limited to, the IL-8 promoter, the metallothionine inducible promoter system, the bacterial lacZYA expression system, the tetracycline expression system, a T7 polymerase system, a bipartite inducible system, and combinations thereof, as disclosed, for example, in Yao et al., *Human Gene Therapy*, 9, 1939–1950 (1998).

One of ordinary skill in the art will appreciate that each promoter drives transcription, and, therefore, RNA molecule production and protein expression, differently with respect to time and amount of protein produced. Thus, a promoter can be selected for use in the method of the present invention by matching its particular pattern of activity with the desired pattern and level of expression. Alternatively, a hybrid promoter (e.g., a CMV-RSV hybrid promoter) can be constructed which combines the desirable aspects of multiple promoters.

Promoters, nucleotide sequences, selectable markers, and the like can be located on the DNA molecule of the recombinant phage vector. Such elements can be present as part of a cassette, either independently or coupled. In the context of the present invention, a "cassette" is a particular nucleotide sequence that possesses functions which facilitate subcloning and recovery of nucleotide sequences (e.g., one or more restriction sites) or expression (e.g., polyadenylation or splice sites) of particular nucleotide sequences.

Moreover, to optimize eukaryotic viral vector production, preferably the DNA molecule of the recombinant phage vector further comprises a polyadenylation site following the coding region of the nucleotide sequence. Also, preferably all of the proper transcription signals (and translation signals, where appropriate) are correctly arranged, such that the nucleotide sequence will be properly expressed in the cells into which it is introduced. If desired, the nucleotide sequence also can incorporate splice sites (i.e., splice acceptor and splice donor sites) to facilitate mRNA production.

The DNA molecule of the recombinant phage vector can further comprise a unique enzyme site. A unique enzyme site is defined herein as at least one unique enzyme site, i.e., one or more unique enzyme sites. Thus, multiple unique enzyme sites (e.g., two or more unique enzyme sites, three or more unique enzyme sites, four or more unique enzyme sites, five or more unique enzyme sites, or even six or more unique enzyme sites) can be used in the context of the present invention. In this regard, the DNA molecule can comprise two or more of the same type of unique enzyme site (e.g., about three or more unique enzyme sites, about four or more unique enzyme sites, or even about five or more unique enzyme sites). Moreover, the DNA molecule can comprise two or more different types of unique enzyme sites. The unique enzyme site functions as the site at which the aforementioned unique enzyme restricts (i.e., nicks or cleaves) the DNA molecule, thereby inducing the production of a eukaryotic viral vector by the eukaryotic cell. Preferably, a unique enzyme site is situated (i.e., located) in a region that is not contained within the eukaryotic viral vector genome. More preferably, a unique enzyme site is situated (i.e., located) in a region that is not contained within the eukaryotic viral vector genome and that is in close proximity to an ITR region (e.g., two ITR regions) of the eukaryotic viral vector genome. Moreover, a unique enzyme site can be situated in a region of the DNA molecule that is not contained within the region of the DNA molecule encoding the eukaryotic viral vector genome and is distinct from (i.e., non-overlapping with) the phage packaging site. Alternatively, the DNA molecule does not contain a unique enzyme site, and the phage packaging site acts as the site at which the aforementioned unique enzyme restricts (i.e., nicks or cleaves) the DNA molecule.

The unique enzyme site can be any suitable unique enzyme site. Preferably, the unique enzyme site is specific to the unique enzyme that is present in the eukaryotic cell. Some, but not all, enzymes that are suitable for use as a unique enzyme are discussed above. For example, the DNA molecule can comprise a unique enzyme site, wherein the unique enzyme site is a nuclease site (e.g., a unique restriction enzyme site) and wherein the unique enzyme is a nuclease (e.g., a unique restriction enzyme) which cleaves the nuclease site. In particular, for example, the DNA molecule can comprise a unique enzyme site, wherein the unique enzyme site is a Pac I site and wherein the unique enzyme is Pac I which cleaves the Pac I site.

An additional, typically different, DNA molecule (e.g., a DNA molecule encoding the unique enzyme or a DNA molecule encoding some other desirable gene product) can be used in the context of the present invention and can be contained within any suitable vector. In this regard, any vector (many of which are known to those of ordinary skill in the art) that has the functional ability to contact a eukaryotic cell, in such a manner that this DNA molecule not contained within the aforementioned recombinant phage vector enters the eukaryotic cell, can be used in the context of the present inventive method. Suitable vectors include, for example, recombinant phage vectors, plasmids, plasmid-liposome complexes, and viral vectors, e.g., adeno-associated virus (AAV)-based vectors, retroviral vectors, herpes simplex virus (HSV)-based vectors, AAV-adenoviral chimeric vectors, and adenovirus-based vectors. These vectors can be prepared using standard recombinant DNA techniques described in, e.g., Sambrook et al., Molecular Cloning, A Laboratory Manual, 2nd edition, Cold Spring Harbor Press, Cold Spring Harbor, N.Y. (1989), and Ausubel et al., Current Protocols in Molecular Biology, Greene Publishing Associates and John Wiley & Sons, New York, N.Y. (1994). The discussion herein of coding sequences, promoters, and other elements with respect to the DNA molecule of the recombinant phage vector also is applicable to this additional DNA molecule not contained within the aforementioned recombinant phage vector. Thus, for example, this additional DNA molecule can encode, and be expressed to produce, the unique enzyme. Indeed, this additional DNA molecule can further comprise a regulatable promoter operably linked to at least the portion of the DNA molecule encoding the unique enzyme.

All of the references cited herein, including patents, patent applications, and publications, are hereby incorporated in their entireties by reference.

While this invention has been described with an emphasis upon preferred embodiments, variations of the preferred embodiments may be used, and the invention may be practiced otherwise than as specifically described herein. Accordingly, this invention includes all modifications encompassed within the spirit and scope of the invention as defined by the following claims.

What is claimed is:

1. A method of producing a eukaryotic viral vector, which method comprises:

contacting a eukaryotic cell, which comprises a genorne and which does not comprise a unique enzyme that nicks or cleaves a DNA molecule, simultaneously or sequentially, in either order, with (i) a unique enzyme that nicks or cleaves a DNA molecule and (ii) a recombinant phage vector, wherein the recombinant phage vector comprises the DNA molecule comprising (a) a eukaryotic viral vector genome comprising a coding sequence, (b) a phage packaging site and a unique enzyme site that are not contained within the eukaryotic viral vector genome, and (c) a promoter that is operably linked to the coding sequence, whereupon the DNA molecule enters the eukaryotic cell and the unique enzyme nicks or cleaves the unique enzyme site in the DNA molecule in the eukaryotic cell, whereupon a eukaryotic viral vector is produced.

2. The method of claim 1, wherein the DNA molecule encodes the unique enzyme and is expressed to produce the unique enzyme.

3. The method of claim 1, wherein said unique enzyme is encoded by and expressed from a second DNA molecule which is not contained within the recombinant phage vector or the genome of the eukaryotic cell, and said contacting comprises contacting said cell with said second DNA molecule.

4. The method of claim 3, wherein said second DNA molecule encoding the unique enzyme is contained within a viral vector.

5. The method of claim 3, wherein said second DNA molecule encoding the unique enzyme further comprises a regulatable promoter operably linked to at least the portion of the DNA molecule encoding the unique enzyme.

6. The method of claim 1, wherein the phage packaging site is a lambda cos site.

7. The method of claim 6, wherein the unique enzyme is lambda terminase, and the lambda terminase cleaves the lambda cos site.

8. The method of claim 1, wherein the eukaryotic viral vector is an adenoviral vector.

9. The method of claim 8, wherein the adenoviral vector is an $E1^-$ adenoviral vector.

10. The method of claim 9, wherein the adenoviral vector is an $E1^-E3^-$ adenoviral vector.

11. The method of claim 10, wherein the adenoviral vector is an E1a $^-$E1b$^-$E3$^-$ adenoviral vector.

12. The method of claim 8, wherein the adenoviral vector is an $E4^-$ adenoviral vector.

13. The method of claim 12, wherein the adenoviral vector is an $E1^-E4^-$ adenoviral vector.

14. The method of claim 13, wherein the adenoviral vector is an $E1^-E3^-E4^-$ adenoviral vector.

15. The method of claim 8, wherein the adenoviral vector is an adenoviral amplicon.

16. The method of claim 1, wherein the coding sequence is a coding sequence of the eukaryotic viral vector genome.

17. The method of claim 1, wherein the coding sequence is a coding sequence not endogenous to the eukaryotic viral vector genome.

18. The method of claim 1, wherein the promoter is a regulatable promoter.

19. The method of claim 1, wherein the recombinant phage vector comprises at least one capsid protein that binds to a membrane receptor on the eukaryotic cell such that the recombinant phage vector infects the eukaryotic cell.

20. The method of claim 19, wherein the recombinant phage vector comprises a nucleic acid sequence that encodes and is expressed to produce a modified D capsid protein.

21. The method of claim 1, wherein the recombinant phage vector is administered in conjunction with a bispecific molecule, which binds to a capsid protein of the recombinant phage vector and to a membrane receptor of the eukaryotic cell, such that the recombinant phage vector infects the eukaryotic cell.

* * * * *